(12) United States Patent
Desesquelle

(10) Patent No.: US 8,962,021 B2
(45) Date of Patent: Feb. 24, 2015

(54) SOLID PHARMACEUTICAL COMPOSITION COMPRISING TELITHROMYCIN

(71) Applicant: Aventis Pharma S.A., Antony (FR)

(72) Inventor: Christian Desesquelle, Soisy Sous Montmorency (FR)

(73) Assignee: Aventis Pharma SA, Paris (FR)

( * ) Notice: Subject to any disclaimer, the term of this patent is extended or adjusted under 35 U.S.C. 154(b) by 0 days.

(21) Appl. No.: 14/014,677

(22) Filed: Aug. 30, 2013

(65) Prior Publication Data

US 2013/0344151 A1    Dec. 26, 2013

Related U.S. Application Data

(63) Continuation of application No. 11/839,719, filed on Aug. 16, 2007, now abandoned, which is a continuation of application No. PCT/FR2006/000411, filed on Feb. 23, 2006.

(30) Foreign Application Priority Data

Feb. 25, 2005 (FR) ...................................... 05 01936

(51) Int. Cl.
| | |
|---|---|
| *A61K 9/20* | (2006.01) |
| *A61K 9/36* | (2006.01) |
| *A61K 31/70* | (2006.01) |
| *A61K 31/706* | (2006.01) |
| *A61K 9/28* | (2006.01) |
| *A61K 31/704* | (2006.01) |

(52) U.S. Cl.
CPC ............. *A61K 31/706* (2013.01); *A61K 9/2054* (2013.01); *A61K 9/2866* (2013.01); *A61K 31/704* (2013.01)

USPC .............................. 424/465; 424/480; 514/29

(58) Field of Classification Search
None
See application file for complete search history.

(56) References Cited

U.S. PATENT DOCUMENTS

| | | |
|---|---|---|
| 2004/0013737 A1 | 1/2004 | Becourt et al. |
| 2004/0091536 A1 | 5/2004 | Meisonnier et al. |
| 2004/0228915 A1 | 11/2004 | Noack et al. |
| 2005/0037983 A1 | 2/2005 | Dinan et al. |
| 2006/0099266 A1 | 5/2006 | Rohra et al. |

FOREIGN PATENT DOCUMENTS

| | | |
|---|---|---|
| FR | 2826274 | 12/2002 |
| WO | WO 2006/090067 | 8/2006 |

OTHER PUBLICATIONS

Ketek Tablets Information, Internet Article [Online] (2004) Retrieved from the Internet, URL:http://www.drugs.com/pdr/KetekTablets.html.
Handbook of Pharm. Excip., (1988), p. 53-55, (Microcrystalline Cellulose).
Handbook of Pharm. Excip., (1988), p. 153, (Lactose Monohydrate).
Scientific Discussion, (codedCPMP/1014/01 and copyrighted by EMEA in 2001; and made available online Jan. 31, 2002), pp. 1-23.

*Primary Examiner* — Robert A Wax
*Assistant Examiner* — Jeffrey T Palenik
(74) *Attorney, Agent, or Firm* — Ronald G. Ort

(57) ABSTRACT

This invention relates to a solid pharmaceutical tablet comprising telithromycin or a salt thereof as an active ingredient in combination with a plasticizing effective amount of a microcrystalline cellulose diluent having a plastic behavior. Optional ingredients include a binder, a disintegrating agent and a lubricant, and the tablet may be optionally coated with a film-coating agent.

11 Claims, 1 Drawing Sheet

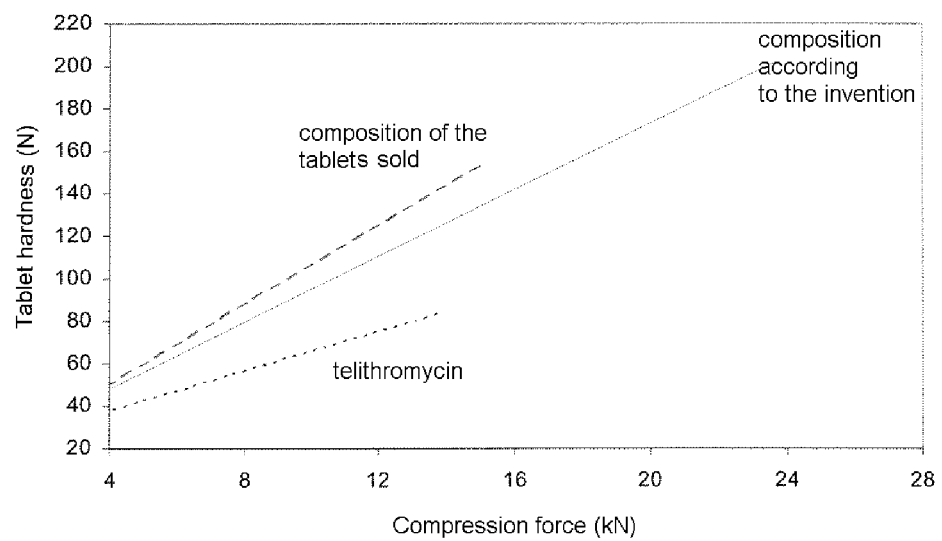

SOLID PHARMACEUTICAL COMPOSITION COMPRISING TELITHROMYCIN

The invention relates to a novel solid pharmaceutical composition of telithromycin that in particular allows facilitated swallowing by the patient.

The unit amount of active ingredient to be administered orally via a solid pharmaceutical composition often makes it necessary to prepare tablets that are of a size such that the swallowing thereof can give many patients, children of course, but not only children, difficulties. In addition, the nature of the active ingredient makes it necessary to add thereto a certain number of excipients that are sometimes themselves in considerable amount in order to ensure the cohesion of the formulation, but also to perform an important, or even essential, function, for example when masking of the taste of the active ingredient is desired. This is most particularly the case for compounds of macrolide/ketolide type, such as telithromycin.

BRIEF DESCRIPTION OF THE DRAWING

FIG. 1 is a graph that shows tablet hardness vs. compression force for tablets prepared in accordance with Example 1.

The active ingredient telithromycin, or 11,12-dideoxy-3-de((2,6-dideoxy-3-C-methyl-3-O-methyl-alpha-L-ribohexopyranosyl)oxy)-6-O-methyl-3-oxo-12,11-(oxycarbonyl-((4-(4-(3-pyridinyl)-$^1$H-imidazol-1-yl)butylimino))-erythromycin, is described in European Patent EP 0 680 967. Oral administration is a favored administration form for this active ingredient having antibiotic properties.

Telithromycin tablets containing a dose of 400 mg and 300 mg are thus currently sold. These tablets contain a proportion of active ingredient of 50% by weight, relative to the total weight of the tablet before coating, and also a considerable proportion of excipient for granulation (close to 30% by weight of lactose), a mixture of excipients for disintegration (close to 13% by weight of a mixture of corn starch in a very high proportion and of sodium croscarmellose in a very low proportion), a low percentage of diluent (between 4 and 5% by weight of microcrystalline cellulose), and a low percentage of binder (less than 2% by weight) and of lubricant (less than 1% by weight), these tablets being coated with a film-coating.

These tablets containing 400 mg and 300 mg of telithromycin thus have a total mass, respectively, of 800 and 600 mg (not including the film-coating) and have an oblong shape with large dimensions, respectively of (18 mm×9 mm) and (13.9 mm×8.7 mm). It can therefore readily be seen that the swallowing of such tablets by patients is sometimes difficult.

It was therefore desirable to achieve a reduction in the size of these telithromycin tablets.

It is possible to consider solving this problem simply by increasing the proportion of active ingredient in the composition of the tablet and therefore, at an equal dose of active ingredient, of reducing the size thereof. However, the telithromycin active ingredient has specific mechanical properties such that this is not possible for the tablets currently sold: the proportion of 50% by weight of telithromycin in the compositions before coating for the tablets sold, as indicated above, constitutes a maximum.

Moreover, besides this problem of tablet size, which is inherent to this specific active ingredient, another drawback related to telithromycin exists, which manifests itself during the implementation of the industrial process for preparing the tablets.

Telithromycin is in fact an active ingredient which is difficult to compress. The result is that the mechanical characteristics of the tablets obtained are not satisfactory, especially for allowing high-throughput production. During the compression process, a tendency for the tablets to split can appear, which results in a high rejection rate of tablets declared to be nonconform due to a defect in appearance related to a lack of cohesion and, consequently, a notable economic loss.

A novel composition for telithromycin tablets has now been found, entirely surprisingly and unexpectedly, by virtue of which it is possible to simultaneously remedy the major drawbacks mentioned above, in particular, firstly, to be able to include a much higher proportion of the telithromycin active ingredient, ranging up to 80% by weight of the tablet excluding film-coating and, consequently, at an equal dosage of active principle, to provide tablets whose size is very substantially reduced and, secondly, to be able to quite significantly increase the breaking strength of the tablet before coating and, consequently, to very substantially reduce, on the industrial scale, the rejection rate of tablets for a defect in appearance related to a lack of cohesion.

A subject of the present invention is thus a solid pharmaceutical composition comprising telithromycin or an addition salt thereof with a pharmaceutically acceptable acid, as an active ingredient, characterized in that it comprises, relative to the total weight of the composition:
  telithromycin or an addition salt thereof with a pharmaceutically acceptable acid, in a proportion of telithromycin of between 0.1 and 80% by weight, and
  at least one diluent having a plastic behavior, in a proportion of 10 to 50% by weight.

Unless otherwise specified, the proportions indicated by weight relative to the total weight of the composition are understood to mean relative to the total weight of the composition without taking into account any possible coating of the latter, in particular with a film-coating.

More particularly, the proportions by weight indicated for the telithromycin active ingredient, whether or not it is present in the form of an addition salt thereof with a pharmaceutically acceptable acid, are proportions calculated by weight of the telithromycin compound relative to the total weight of the composition without taking into account any possible coating of the latter, in particular with a film-coating.

As possible addition salt of telithromycin with a pharmaceutically acceptable acid, mention may in particular be made of addition salts with inorganic or organic acids, especially the salts formed with acetic acid, propionic acid, trifluoroacetic acid, maleic acid, tartaric acid, methanesulfonic acid, benzenesulfonic acid, p-toluenesulfonic acid, hydrochloric acid, hydrobromic acid, hydroiodic acid, sulfuric acid or phosphoric acid, and more particularly stearic acid, ethylsuccinic acid or laurylsulfuric acid.

The composition according to the invention preferably comprises telithromycin, or an addition salt thereof with a pharmaceutically acceptable acid, in a proportion of telithromycin of between 50 and 80% by weight, more particularly between 60 and 80% by weight, and even more particularly between 60 and 70% by weight, relative to the total weight of the composition.

According to the present invention, it has in particular been noted, surprisingly, that, by very substantially increasing the proportion of one of the excipients in the composition already sold for telithromycin tablets, indicated above, to the detriment of two other specific excipients of this same already known composition, it is possible both to increase the proportion of the telithromycin active ingredient, up to at least 80% by weight, while at the same time improving the breaking strength of the tablets, in particular during the composition compression process. Without wishing to be held to any theory, it appears that the very substantial increase in the proportion of this specific excipient, i.e. the diluent, in particular microcrystalline cellulose, to the detriment however of two other specific excipients already present in this same already known composition, i.e. the lactose and the corn starch, would make it possible to confer on this diluent a plasticizing function that is determinant for the mechanical properties of the telithromycin composition, in particular during its compression, hence this expression "diluent having a plastic behavior".

The expression "diluent having a plastic behavior" is thus intended to mean, according to the invention, any excipient known to those skilled in the art that exhibits both this function of diluent and, at a proportion by weight of between 10 and 50% by weight, this plasticizing function with respect to the telithromycin composition, in particular during the compression thereof.

It has, moreover, been possible to note that this result, which is as advantageous as it is unexpected, is further improved by acting on the other excipients also present in the composition of the tablets sold.

Thus, preferably, the pharmaceutical composition according to the invention also comprises, relative to the total weight of the composition:
  at least one binder, in a proportion of 2.5 to 3.5% by weight,
  at least one disintegrating agent, in a proportion of 3 to 8% by weight, and
  at least one lubricant, in a proportion of 0.6 to 1% by weight.

Preferably, the diluent having a plastic behavior is present in a proportion of between 20 and 30% by weight, relative to the total weight of the composition according to the invention.

More particularly, the pharmaceutical composition according to the present invention is characterized in that it comprises, relative to the total weight of the composition:
  telithromycin, or an addition salt thereof with a pharmaceutically acceptable acid, in a proportion of telithromycin of between 50 and 80% by weight, more particularly between 60 and 80% by weight, and even more particularly between 60 and 70% by weight,
  at least one diluent having a plastic behavior, in a proportion of 20 to 30% by weight,
  at least one binder, in a proportion of 2.8 to 3% by weight,
  at least one disintegrating agent, in a proportion of 3.5 to 6% by weight, and
  at least one lubricant, in a proportion of 0.6 to 1% by weight.

According to a particularly preferred embodiment of the present invention, the diluent having a plastic behavior as defined above is microcrystalline cellulose.

According to one particular embodiment, the pharmaceutical composition according to the invention is characterized in that:
  the binder is chosen from the group consisting of povidone K25, povidone K30, copovidone and hydroxypropylcellulose, and mixtures thereof,
  the disintegrating agent is chosen from the group consisting of sodium croscarmellose, crospovidone and sodium carboxymethyl starch, and mixtures thereof,
  the lubricant is chosen from the group consisting of magnesium stearate and micronized stearic acid, and mixtures thereof.

Even more particularly, the pharmaceutical composition according to the invention is characterized in that:
  the binder is chosen from the group consisting of povidone K25 and povidone K30, and mixtures thereof,
  the disintegrating agent is sodium croscarmellose, and
  the lubricant is magnesium stearate.

Finally, according to a most particularly preferred embodiment, the pharmaceutical composition according to the invention is characterized in that it comprises, relative to the total weight of the composition:
  from 60 to 70% by weight of telithromycin,
  from 20 to 30% by weight of microcrystalline cellulose,
  from 2.8 to 3% by weight of povidone chosen from the group consisting of povidone K25 and povidone K30, and mixtures thereof,
  from 3.5 to 6% by weight of sodium croscarmellose, and
  from 0.6 to 1% by weight of magnesium stearate.

The solid composition according to the invention can, of course, consist of the composition intended to be subjected to the compression process, i.e. the composition resulting from this process. Thus, in particular, the pharmaceutical composition according to the invention is characterized in that it is in the form of a tablet.

The telithromycin can in particular be present in the composition according to the invention in the form of granulated material obtained by granulation, in particular by wet granulation, the pharmaceutical composition according to the invention thus comprising telithromycin granulated material dispersed in an external phase comprising other components of the composition, before or after the compression process. In particular, the telithromycin granulated material also comprises said binder and the external phase comprises said disintegrating agent and lubricant. It has been possible to observe that the diluent having a plastic behavior can be present in said telithromycin granulated material and said external phase.

When the composition has been subjected to the compression process, the tablet which results therefrom can also be subjected in particular to a coating operation, in particular with a film-coating according to operating conditions well known to those skilled in the art. Thus, in particular, the pharmaceutical composition according to the invention is characterized in that it is in the form of a tablet and in that it is coated with a film-coating. More particularly, this film-coating can comprise at least one component chosen from the group consisting of hypromellose, polyethylene glycol, titanium dioxide, talc, yellow iron oxide and red iron oxide, and mixtures thereof.

Finally, the pharmaceutical composition according to the invention preferably comprises from 50 mg to 600 mg of telithromycin, in particular 400 mg or alternatively 300 mg of telithromycin.

The novel composition according to the invention thus makes it possible, for dosages of telithromycin active ingredient of 400 and 300 mg, i.e. identical to that of the existing tablets, to have reduced dimensions. The tablets according to the invention have sizes which are, respectively, (13.9 mm×8.7 mm) and (12.5 mm×7.8 mm).

In the end, the composition according to the invention can therefore advantageously have a reduced size, in the form of a tablet, at a telithromycin dosage that is nevertheless equal, compared to the tablets of the composition sold, which in itself provides a very important advantage both in terms of patient adherence and in terms of reduction of the production costs of the finished pharmaceutical product. What is more, as indicated in the study hereinafter, these reduced-size tablets exhibit better hardness, which, on the industrial scale, is reflected by a very advantageous decrease in the rejection rate of tablets for a defect in appearance related to a lack of cohesion, for example from 2% to 0.02% for 300 mg telithromycin tablets.

The following examples are intended to illustrate the present invention and should in no way be interpreted as being able to limit the scope thereof.

FIG. 1 represents three dashed curves showing the hardness (in N) of three tablets as a function of the compression force (in kN) according to the breaking strength test described hereinafter. The curve with the smallest dashes corresponds to the test on the composition according to the invention prepared in Example 1.1 (before compression and film-coating), the curve with the largest dashes corresponds to the test on the composition of the tablets sold (before compression and film-coating), and the curve with intermediate-sized dashes corresponds to the test on the powder of telithromycin active ingredient.

EXAMPLE 1

Tablets Containing 400 mg of Telithromycin

Telithromycin-based tablets, the composition of which is reported in the following Table 1 (composition according to the invention, coated with a film-coating), are prepared.

For this, the procedure is carried out in the following way:
1.1 Preparation of the Tablet 133.00 kg of telithromycin and 39.20 kg of microcrystalline cellulose (Avicel PH 101) are introduced into a mixer-granulator and mixed for 5 minutes.

60.60 kg of purified water and 6.00 kg of povidone K25 are mixed separately, and the clear solution obtained is then poured onto the mixture of powders obtained above, with stirring maintained.

The wet granulated material thus obtained is broken up using a CoMil rotary calibrating device equipped with a screen having a 9.5 mm mesh size, and the broken up granulated material is then transferred into a drying tank. It is maintained therein at 60° C. in a fluidized air bed dryer until a residual solvation of less than 2% is obtained.

The dried granulated material is then sieved using a calibrating device equipped with a screen having a 1.6 mm mesh size.

12.000 kg of microcrystalline cellulose (Avicel PH 101) and 7.980 kg of sodium croscarmellose are added to the calibrated granulated material and the mixture is then maintained without stirring for 10 minutes.

1.320 kg of magnesium stearate are then added and the mixture is then kept stirring for 4 minutes.

The granulated material thus obtained is then compressed using a compression press having the equipment required for the desired dosage of 400 mg.

Tablets having the composition indicated in Table 1 (without the film-coating), the size of which is (13.9 mm×8.7 mm) instead of (18 mm×9 mm) for the tablets sold, are thus obtained.
2.2 Film-Coating of the Tablet A film-coating solution is prepared as follows.

The following components are introduced into 133.5 kg of purified water, slowly, with stirring, one by one:
  24.000 kg of hydroxypropylmethylcellulose 6 cP (hypromellose 6 cP),
  1.050 kg of polyethylene glycol 8000,
  1.800 kg of talc,
  5.100 kg of titanium dioxide,
  0.750 kg of yellow iron oxide,
  0.150 kg of red iron oxide, and the mixture is kept stirring until a homogeneous suspension is obtained.

A further 133.5 kg of purified water are then added and the stirring is then continued for 5 minutes.

The suspension obtained is used to film-coat the tablets obtained above, in an Accela Cota film-coating pan.

TABLE 1

Composition for film-coated telithromycin tablets

| Component | Proportion (% by weight; with film-coating) |
|---|---|
| Active ingredient | |
| telithromycin | 65.20% (400 mg) |
| Excipients | |
| microcrystalline cellulose[1] | 25.10% |
| Sodium croscarmellose[2] | 3.91% |
| povidone K25[3] | 2.93% |
| magnesium stearate | 0.65% |
| Film-coating | |
| hypromellose 6 cP[4] | 1.62% |
| polyethylene glycol 8000[5] | 0.07% |
| titanium dioxide | 0.34% |
| talc | 0.12% |
| yellow iron oxide | 0.05% |
| red iron oxide | 0.01% |
| Total (with film-coating) | 100.00% |

[1]Avicel PH 1001 sold by FMC
[2]Ac-Di-Sol sold by FMC
[3]Kollidon 25 sold by BASF
[4]Pharmacoat 606 sold by Shin-Etsu
[5]Polyglycol 8000P sold by Hoechst Study of the Breaking Strength of the Composition According to the Invention in the Form of a Tablet The compressibility of a powder is evaluated by its ability to form a compact when it is subjected to a pressure. This is carried out in the context of the method illustrated above, using an alternating compression press equipped with punches bearing strain gauges. An amplification system and a converter make it possible to register, at any moment, the forces applied during the compression cycle. At the end of the process, the breaking strength of the tablet formed is measured by means of a hardness bench. A measurement of breaking strength or "hardness" of the tablet (in N) is thus obtained for a given compression force (in kN). For a powder to be tested, this process is repeated several times so as to be able to plot a curve such as those of FIG. 1.

Comparative trials were thus carried out on the powder of the telithromycin active ingredient, on the composition used for the production of the tablets sold, before compression and film-coating (containing 50% by weight of telithromycin without film-coating) and on the composition according to the invention prepared in Example 1.1 above, before compression and film-coating (containing 66.7% by weight of telithromycin without film-coating).

The results of these comparative trials are reported in the form of the three respective curves in FIG. 1.

These comparative trials show the improvement provided by the composition according to the invention, illustrated by the difference in length of the curves which attest to the increase in cohesion of the tablets proportionally to the pressure exerted. Beyond the curve, the hardnesses of the tablets stagnate or decrease, indicating cleavage phenomena.

On the industrial scale, on tablets that are similar but contain doses of 300 mg of telithromycin, it was possible to observe that this improvement is reflected by a very advantageous reduction from 2% to 0.02% in the rejection rate of tablets for a defect in appearance related to a lack of cohesion.

What is claimed is:

1. A solid pharmaceutical tablet comprising telithromycin or an addition salt thereof with a pharmaceutically acceptable acid, as an active ingredient, which comprises, relative to the total weight of the tablet, a mixture of:
   between about 50 and 80% by weight of telithromycin or an addition salt thereof with a pharmaceutically acceptable acid, and
   a plasticizing effective amount of about 20 to 30% by weight of at least one microcrystalline cellulose diluent having a plastic behavior.

2. The tablet of claim 1, which also comprises:
   about 2.5 to 3.5% by weight of at least one binder,
   about 3 to 8% by weight of at least one disintegrating agent, and
   about 0.6 to 1% by weight of at least one lubricant.

3. The tablet of claim 2, which comprises:
   between about 60 and 80% by weight of telithromycin or an addition salt thereof with a pharmaceutically acceptable acid,
   about 20 to 30% by weight of said at least one diluent having a plastic behavior,
   about 2.8 to 3% by weight of at least one binder,
   about 3.5 to 6% by weight of at least one disintegrating agent, and
   about 0.6 to 1% by weight of at least one lubricant.

4. The tablet of claim 2, wherein:
   the binder is selected from the group consisting of povidone K25, povidone K30, copovidone, hydroxypropylcellulose, and mixtures thereof,
   the disintegrating agent is selected from the group consisting of sodium croscarmellose, crospovidone, sodium carboxymethyl starch, and mixtures thereof, and;
   the lubricant is selected from the group consisting of magnesium stearate, micronized stearic acid, and mixtures thereof.

5. The tablet of claim 4, wherein:
   the binder is selected from the group consisting of povidone K25, povidone K30, and mixtures thereof,
   the disintegrating agent is sodium croscarmellose, and
   the lubricant is magnesium stearate.

6. The tablet of claim 5, which comprises:
   from about 60 to 70% by weight of telithromycin,
   from about 20 to 30% by weight of microcrystalline cellulose,
   from about 2.8 to 3% by weight of a povidone selected from the group consisting of povidone K25, povidone K30, and mixtures thereof,
   from about 3.5 to 6% by weight of sodium croscarmellose, and
   from about 0.6 to 1% by weight of magnesium stearate.

7. The tablet of claim 1 wherein the tablet is coated with a film-coating agent.

8. The tablet of claim 7, wherein said film-coating agent comprises at least one component selected from the group consisting of hypromellose, polyethylene glycol, titanium dioxide, talc, yellow iron oxide, red iron oxide, and mixtures thereof.

9. The tablet of claim 1, which comprises from about 50 mg to 600 mg of telithromycin.

10. The tablet of claim 9, which comprises about 400 mg of telithromycin.

11. The tablet of claim 9, which comprises about 300 mg of telithromycin.

* * * * *